(12) United States Patent
Lampilas et al.

(10) Patent No.: US 8,063,219 B2
(45) Date of Patent: Nov. 22, 2011

(54) NITROGENOUS HETEROCYCLIC COMPOUNDS, PREPARATION THEREOF AND USE THEREOF AS ANTIBACTERIAL MEDICAMENTS

(75) Inventors: Maxime Lampilas, Paris (FR); David Alun Rowlands, Poissy (FR); Adel Kebsi, Thiais (FR); Benoit Ledoussal, Bouleurs (FR); Camille Pierres, Paris (FR)

(73) Assignee: Novexel, Romainville (FR)

( * ) Notice: Subject to any disclaimer, the term of this patent is extended or adjusted under 35 U.S.C. 154(b) by 0 days.

(21) Appl. No.: 12/595,120

(22) PCT Filed: Apr. 11, 2008

(86) PCT No.: PCT/FR2008/000509
§ 371 (c)(1),
(2), (4) Date: Feb. 2, 2010

(87) PCT Pub. No.: WO2008/142285
PCT Pub. Date: Nov. 27, 2008

(65) Prior Publication Data
US 2010/0137355 A1    Jun. 3, 2010

(30) Foreign Application Priority Data
Apr. 12, 2007 (FR) ...................................... 07 02663

(51) Int. Cl.
*A61K 31/437* (2006.01)
*A61P 31/04* (2006.01)
*C07D 471/04* (2006.01)

(52) U.S. Cl. ....................................... 546/121; 514/300
(58) Field of Classification Search .................. None
See application file for complete search history.

(56) References Cited

OTHER PUBLICATIONS

Silverman, The Organic Chemistry of Drug Design and Drug Action, Academic Press (1992).*

Written Opinion of the International Searching Authority, International Application No. PCT/FR2008/000509, date of mailing, Oct. 13, 2009 and attached English Translation.
Written Opinion of the International Searching Authority, International Application No. PCT/FR2008/000509, date of mailing, Nov. 3, 2009 and attached English Translation.

* cited by examiner

*Primary Examiner* — Janet Andres
*Assistant Examiner* — Timothy R Rozof
(74) *Attorney, Agent, or Firm* — Hamilton, Brook, Smith & Reynolds, P.C.

(57) ABSTRACT

The invention concerns nitrogenated heterocyclic compounds, their preparation and use as antibacterial drugs, compounds of general formula (I)

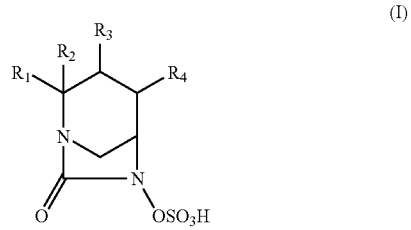

wherein $R_1$ represents a $(CH_2)n\text{-}NHR_2$ or $(CH_2)n\text{-}NHR$ radical, where R is a $(C_1\text{-}C_6)$ alkyl and n is equal to 1 or 2;
  $R_2$ represents a hydrogen atom;
  $R_3$ and $R_4$ together form an aromatic nitrogenated heterocycle with 5 apexes with 1, 2 or 3 nitrogen atoms optionally substituted by one or several R' groups, R' being selected in the group composed of a hydrogen atom and alkyl radicals with 1 to 6 carbon atoms;
  in free form, as zwitterions, and in the form of salts of pharmaceutically acceptable inorganic or organic bases and acids.

20 Claims, No Drawings

NITROGENOUS HETEROCYCLIC COMPOUNDS, PREPARATION THEREOF AND USE THEREOF AS ANTIBACTERIAL MEDICAMENTS

This application is the U.S. National Stage of International Application No. PCT/FR2008/000509, filed Apr. 11, 2008, which designates the U.S., published in French, and claims priority under 35 U.S.C. §§119 or 365(c) to France Application No. 0702663, filed Apr. 12, 2007. The entire teachings of the above applications are incorporated herein by reference.

The invention concerns nitrogenated heterocyclic compounds, their preparation and use as antibacterial drugs.

The application WO 02/100860 describes compounds with the following formula:

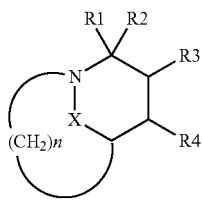

wherein:
a) either R1 represents a hydrogen atom, a COOH, CN, COOR, $(CH_2)_{n'}R_5$, $CONR_6R_7$ radical or

R is selected from the group composed of an alkyl radical with 1 to 6 carbon atoms, optionally substituted by a pyridyl radical, a —$CH_2$-alkenyl radical with a total of 3 to 9 carbon atoms, a (poly)alkoxyl radical with 1 to 4 oxygen atoms and 3 to 10 carbon atoms, an aryl radical with 6 to 10 carbon atoms or aralkyl radical with 7 to 11 carbon atoms, the aryl or aralkyl radical nucleus being optionally substituted by an OH, $NH_2$, $NO_2$ radical, an alkyl radical with 1 to 6 carbon atoms, an alkoxy radical with 1 to 6 carbon atoms or by one or several halogen atoms, $R_5$ is selected from a group composed of a COOH, CN, OH, $NH_2$, CO—$NR_6R_7$, COOR, OR, OCOH, OCOR, OCOOR, OCONHR, $OCONH_2$, $OSO_2R$, NHR, NHCOR, NHCOH, $NHSO_2R$, NH—COOR, NH—CO—NHR, NH—CO—$NH_2$ or $N_3$ radical, where R is defined as above, $R_6$ and $R_7$, identical or different, are selected from the group composed of a hydrogen atom, an alkyl radical with 1 to 6 carbon atoms, an aryl radical with 6 to 10 carbon atoms, an aralkyl radical with 7 to 11 carbon atoms and an alkyl radical with 1 to 6 carbon atoms substituted by a pyridyl radical, n' is equal to 1 or 2, $R_3$ and $R_4$ together form a phenyl or aromatic heterocycle with 5 or 6 apexes including 1 to 4 heteroatoms selected from among nitrogen, oxygen and sulphur, and optionally substituted by one or several R' groups, R' being selected from the group composed of a hydrogen atom and the alkyl radicals with 1 to 6 carbon atoms, optionally substituted by one or several hydroxyl, oxo, halogen or cyano radicals or by a nitro, alkenyl with 2 to 6 carbon atoms, halogen, amino, OH, protected OH, —OR, —NHCOH, —NHCOR, NHCOOR, COOH, —COOR, —$C(C_6H_5)_3$ and —$CH_2$—$CH_2$—$S(O)_m$—R radicals, where R is as defined above and m is equal to 0, 1 or 2, b) or $R_4$ represents a hydrogen atom or a $(CH_2)_{n'1}R_5$ group, where n'1 is equal to 0, 1 or 2 and $R_5$ is as defined above, and $R_1$ and $R_3$ together form a phenyl or a heterocycle optionally substituted, as defined above, in both cases a) and b)

$R_2$ is selected from the group composed of a hydrogen atom, a halogen atom and the R, $S(O)_mR$, OR, NHCOR, NHCOOR and $NHSO_2R$ radicals, where m and R are as defined above, X represents a divalent group —C(O)—B— bonded to the nitrogen atom by the carbon atom, B represents a divalent group —O—$(CH_2)_{n''}$— bonded to the carbonyl by the oxygen atom, a —$NR_8$—$(CH_2)_{n''}$— or —$NR_8$—O— group bonded to the carbonyl by the nitrogen atom, n'' is equal to 0 or 1 and $R_8$ is selected from the group composed of a hydrogen atom, an OH, R, OR, Y, OY, $Y_1$, $OY_1$, $Y_2$, $OY_2$, $Y_3$, O—$CH_2$—$CH_2$—$S(O)m$-R, $SiRaRbRc$ and $OSiRaRbRc$ radical, Ra, Rb and Rc individually representing a linear or branched alkyl radical with 1 to 6 carbon atoms or an aryl radical with 6 to 10 carbon atoms, and where R and m are defined as above.

Y is selected in the group composed of the COR, COOR, $CONH_2$, CONHR, CONHOH, $CONHSO_2R$, $CH_2COOH$, $CH_2COOR$, $CH_2CONHOH$, $CH_2CONHCN$, $CH_2$-tetrazole, protected $CH_2$-tetrazole, $CH_2SO_3H$, $CH_2SO_2R$, $CH_2PO(OR)_2$, $CH_2PO(OR)(OH)$, $CH_2PO(R)(OH)$ and $CH_2PO(OH)_2$ radicals, $Y_1$ is selected from the group composed of the $SO_2R$, $SO_2NHCOH$, $SO_2NHCOR$, $SO_2NHCOOR$, $SO_2NHCONHR$, $SO_2NHCONH_2$ and $SO_3H$ radicals, $Y_2$ is selected from the group composed of the $PO(OH)_2$, $PO(OR)_2$, PO(OH)(OR) and PO(OH)(R) radicals, $Y_3$ is selected from the group composed of the radicals tetrazole, tetrazole substituted by the radical R, squarate, NH or NR tetrazole, NH or NR tetrazole substituted by the radical R, $NHSO_2R$ and $NRSO_2R$, where R is defined as above, n is equal to 1 or 2, as well as the salts of these compounds with inorganic or organic bases or acids.

The asymmetric carbon atoms contained in the compounds of formula (I) can independently from each other present the configuration R, S or RS and the compounds of formula (I) are therefore in the form of pure enantiomers or pure diastereoisomers or in the form or a mixture of enantiomers notably of racemates, or mixtures of diastereoisomers.

Further, since, on the one hand, the substituents $R_1$, $R_2$, or $R_4$ taken individually and, on the other hand, X can be in the cis and/or trans position to the ring onto which they are bonded, compounds of formula (I) are in the form of cis or trans isomers or mixtures.

Moreover, application WO 04/052891 describes the related compounds.

The applicant has discovered that among the compounds described in the application WO 02/100860, certain particular compounds, none of which are described in the experimental part of these applications, possess quite unexpected antibacterial properties.

The unique nature of the compounds of the invention lies in the fact that they present an excellent activity against *Pseudomonas aeruginosa*, a bacterial strain frequently encountered in nosocomial infections and in patients suffering from cystic fibrosis.

This interesting and unexpected activity is not present in the compounds prepared in the application WO 02/100860 containing $R_1$ groups other than those of the compounds of the invention. It is illustrated below in the part describing the experiments.

Furthermore, the compounds of the invention have been shown to be active on models of animal infection, including on strains usually resistant to the commonly used antibiotics. The compounds of the invention are able to counteract the main resistance mechanisms of bacteria which are β-lactamases, efflux pumps and porin mutations.

The compounds of the invention are compounds with the formula below, wherein $R_2$ represents an atom of hydrogen, $R_3$ and $R_4$ together form an aromatic nitrogenated heterocycle with 5 apexes, X represents a divalent group —C(O)—$NR_8$— wherein $R_8$ is a —$OY_1$ radical, wherein $Y_1$ is a —$SO_3H$, radical, and above all:

$R_1$ represents an alkyl radical substituted by an amino or alkylamino radical.

Therefore the object of the invention is compounds with the general formula (I)

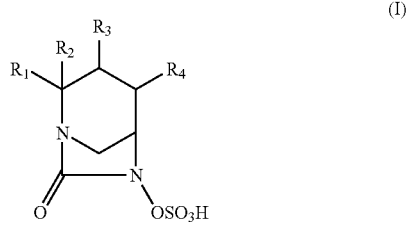

(I)

wherein $R_1$ represents a $(CH_2)_n$—$NH_2$ or $(CH_2)_n$—NHR radical, where R is a ($C_1$-$C_6$) alkyl and n is equal to 1 or 2;

$R_2$ represents a hydrogen atom;

$R_3$ and $R_4$ together form an aromatic nitrogenated heterocycle with 5 apexes with 1, 2 or 3 nitrogen atoms optionally substituted by one or several R' groups, R' being selected in the group composed of a hydrogen atom and the alkyl radicals with 1 to 6 carbon atoms;

in free form, as zwitterions, and in the form of salts of pharmaceutically acceptable inorganic or organic bases and acids.

The expression "alkyl radical with 1 to 6 carbon atoms" as used herein is understood to mean notably the methyl, ethyl, propyl, isopropyl radical, and the linear or branched pentyl or hexyl radicals.

The expression "alkenyl radical with 2 to 6 carbon atoms" as used herein is understood to mean notably the allyl radical and liner or branched butenyl, pentenyl and hexenyl radicals.

The term "aromatic heterocycle" as used herein is understood to mean notably those selected from the following list, the two bonds symbolising the junction with the nitrogenated ring ($R_3R_4$):

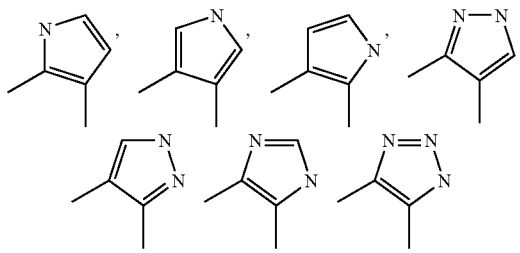

Among the acid salts of the products of formula (I), mention can be made, among other things, of those formed with inorganic acids, such as hydrochloric, hydrobromic, hydroiodic, sulphuric or phosphoric acid or with organic acids such as formic, acetic, trifluoroacetic, propionic, benzoic, maleic, fumaric, succinic, tartric, citric, oxalic, glyoxylic, aspartic, alkanesulphonic acids, such as methane and ethane sulphonic acid, arylsulphonic acids such as benzene and paratoluenesulphonic acid.

Among the basic salts of the products of formula (I), mention can be made, among other things, of those formed with inorganic bases such as, for example, sodium, potassium, lithium, calcium, magnesium or ammonium hydroxide or with organic bases such as, for example, methylamine, propylamine, trimethylamine, diethylamine, triethylamine, N,N-dimethylethanolamine, tris(hydroxymethyl)amino methane, ethanolamine, pyridine, picoline, dicyclohexylamine, morpholine, benzylamine, procaine, lysine, arginine, histidine, N-methylglucamine, or phosphonium salts, such as alkyl-phosphonium, aryl-phosphoniums, alkyl-aryl-phosphonium, alkenyl-aryl-phosphonium or quaternary ammonium salts such as the tetra-n-butyl-ammonium salt.

Among the compounds of formula (I), a notable object of the invention are the compounds wherein $R_3$ and $R_4$ together form a pyrazolyl or triazolyl heterocycle, optionally substituted.

Among the compounds of formula (I), a notable object of the invention are the compounds wherein R1 is selected in the group composed of the groups $(CH_2)_n$—$NH_2$ and $(CH_2)_n$—$NHCH_3$, where n is as defined above, the heterocycle formed by $R_3$ and $R_4$ is substituted by a ($C_1$-$C_6$) alkyl radical.

Among the compounds of formula (I), a particular object of the invention are the compounds wherein R1 represents a $CH_2)_n$—$NH_2$ or $(CH_2)_n$—$NHCH_3$ radical, where n is as defined above and $R_3$ and $R_4$ together form a pyrazolyl ring substituted by a ($C_1$-$C_6$) alkyl radical.

Among the compounds of formula (I), a very particular object of the invention is
- trans 8-(aminomethyl)-4,8-dihydro-1-methyl-6-oxo-5-(sulphooxy)-4,7-methano-7H-pyrazolo[3,4-e][1,3]diazepin-6(5H)-one,
- trans 8-(aminomethyl)-4,8-dihydro-6-oxo-5-(sulphooxy)-4,7-methano-7H-pyrazolo[3,4-e][1,3]diazepin-6(5H)-one and
- trans 8-(methylaminomethyl)-4,8-dihydro-6-oxo-5-(sulphooxy)-4,7-methano-7H-pyrazolo[3,4-e][1,3]diazepin-6(5H)-one, in free form, as a zwitterion, and salts with pharmaceutically acceptable inorganic or organic bases and acids.

Another object of the invention is a method enabling the preparation of compounds of formula (I).

This method is characterised in that it comprises:
a) a step during which a compound of formula (II) is made to react with a carbonylating agent, if necessary in the presence of a base:

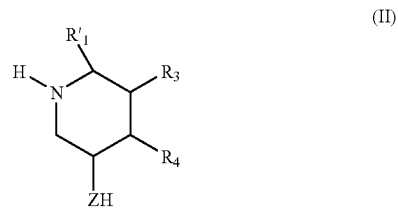

(II)

wherein:

R'₁ represents a CN, protected COOH, COOR or (CH₂)ₙR'₅ radical,

R'₅ is a protected OH, CN NH₂ or protected NHR, protected CO₂H, CO₂R radical n, R, R₃ and R₄ are as defined above, the aminoalkyl substituents optionally present on the heterocycle formed by R₃ and R₄ then being protected if necessary, ZH represents a protected —NHOH group, with the end of obtaining an intermediate compound with the formula (III):

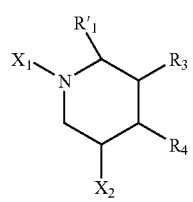

wherein:

R'₁, R₃ and R₄ have the same meanings as above and either X₁ is a hydrogen atom or a protecting group and X₂ represents a —Z—CO—X₃ group, X₃ representing the rest of the carbonylating agent, or X₂ is a —ZH group and X1 represents a CO—X₃ group, X₃ being defined as above;

b) a step during which the intermediate obtained above is cyclised in the presence of a base;

and in that:

c) if necessary, step a) is preceded and/or step b) is followed by one or several of the following reactions, in an appropriate order:

protection of the reactive functions,
deprotection of the reactive functions,
esterification
saponification,
sulphatation,
ester reduction,
alkylation,
carbamoylation,
formation of an azido group,
reduction of an azido into an amine,
salification,
ion exchange,
dividing or separating the diastereoisomers.

As a carbonylating agent, a reagent such as phosgene, diphosgene, triphosgene, an aryl chloroformiate such as phenyl or p-nitrophenyl chloroformiate, a aralkyl chloroformiate such as benzyl chloroformiate, an alkyl or alkenyl chloroformiate such as methyl or allyl chloroformiate, an alkyl dicarbonate such as tert-butyl dicarbonate, carbonyl-diimidazol and their mixtures can be used, disphosgene being preferred.

The reaction preferably takes places in the presence of a base or a mixture of bases that neutralise the acid formed. The base can notably be an amine such as triethylamine, diisopropylethylamine, pyridine, dimethylaminopyridine. However, it is also possible to operate using the formula II starting product as a base. In that case an excess is used.

If necessary, the formula II product is used in the form of an acid salt, for example a hydrochloride or a trifluoroacetate.

As a base in step b), it is also possible to use amines, or hydrides, alcoholates, amides or carbonates of alkaline or alkaline-earth metals.

Amines can be selected for example from the list above.

As a hydride, sodium or potassium hydride can notably be used.

As an alkali metal alcoholate, preferably potassium t-butylate is used.

As an alkali metal amide, lithium bis(trimethylsilyl)amide can notably be used.

As a carbonate, sodium or potassium carbonate or bicarbonate can notably be used.

If necessary, the intermediate with the formula III can be obtained in the form of an acid salt generated during the carbonylation reaction and notably a hydrochloride. It is then used in the cyclisation reaction in this form.

In preference, the cyclisation is carried out without isolating the intermediate with the formula III.

The reactions mentioned in step c) are generally conventional reactions, well known to those skilled in the art. Examples of the conditions used are described in the application WO 02/100860 and also in the application 04/052891.

The reactive functions that need protecting, if necessary, are the carboxylic acid, amine, amide, hydroxy and hydroxylamine functions.

The protection of the acid function is notably provided in the form of alkyl esters, allyl, benzyl, benzhydryl or p-nitrobenzyl esters.

The deprotection is carried out by saponification, acid hydrolysis, hydrogenolysis or cleavage using soluble Palladium O complexes.

Examples of these protections and deprotections are supplied in the application WO 02/100860.

The protection of amines, heterocyclic nitrogens and amides is notably provided, depending on the case, in the form of benzyl or tritylated derivatives, in the form of carbamates, notably allyl, benzyl, phenyl or tertbutyl carbamates, or else in the form of silylated derivatives such as tert-butyl dimethyl, trimethyl, triphenyl or diphenyl tertbutyl-silyl derivatives, or phenylsulphonylalkyl or cyanoalkyl derivatives.

The deprotection is carried out, depending on the nature of the protecting group, by sodium or lithium in liquid ammoniac, by hydrogenolysis or using soluble Palladium O complexes, by the action of an acid, or the action of tetrabutylammonium fluoride or strong bases such as sodium hydride or potassium t-butylate.

The protection of hydroxylamines is carried out notably in the form of benzyl or allyl ethers.

The cleaving of ethers is carried out by hydrogenolysis or using soluble Palladium O complexes.

The protection of alcohols and phenols is carried out in the conventional way, in the form of ethers, esters or carbonates. The ethers can be alkyl or alkoxyalkyl ethers, preferably methyl or methoxyehtoxymethyl ethers, aryl ethers or preferably aralkyl ethers, for example benzyl ethers, or silylated ethers, for example silylated derivatives mentioned above. The esters can be any cleavable ester known to those skilled in the art and preferably acetate, propionate, benzoate or p-nitrobenzoate. The carbonates can be for example methyl, tertbutyl, allyl, benzyl or p-nitrobenzyl carbonates.

The deprotection is carried out by means known to those skilled in the art, notably saponification, hydrogenolysis, cleavage by soluble Palladium O complexes, hydrolysis in an acid medium or, for sylilated derivatives, treating with tetrabutylammonium fluoride.

Examples are given in the part describing the experiments.

The sulphatation reaction is carried out by action of the $SO_3$-amines such as $SO_3$-pyridine or $SO_3$-dimethylformamide, working in pyridine, and the salt formed, for example the pyridine salt can then be exchanged with for example a salt of another amine, a quaternary ammonium or an alkali metal. An example is given in the part describing the experiments.

The alkylation reaction is carried out by action on the hydroxylated derivatives, ester or ketone enolates, heterocyclic amines or nitrogens, depending on the case, of an alkyl sulphate or an alkyl halide or a substituted alkyl, notably by a free or esterified carboxy radical. Alkylation reactions can also be carried out by reducing amination.

The salification by acids is carried out if necessary by the addition of an acid to the soluble phase of the compound. The salification by bases of the sulphooxy function can be carried out using the pyridinium salt obtained during the action of the $SO_3$-pyridine complex and other salts are obtained from this pyridinium salt. Ion exchange on resin can also be carried out.

The carbamoylation reaction can be carried out by using a chloroformiate or a reactive of the Boc-ON type then an amine or, if necessary, an ammoniac.

An azido group can be introduced for example by the action of sodium azotide on a mesylate type intermediate or by reactions of the Mitsunobu type.

The reduction of an azide group can be carried out by the action of trialkyl or triarylphosphine.

The separation of enantiomers and diastereoisomers can be carried out according to techniques known to those skilled in the art, notably chromatography.

Apart from the methods described above, compounds of the formula (I) can be obtained by methods that initially use a compound of formula (II) in which $R'_1$, $R_3$, $R_4$ and HZ have values that lead directly (without transformation) to those of the compounds that one wishes to prepare. If necessary, the compounds of these groups that would include reactive functions such as those mentioned above are protected, and the deprotection takes place after the step b) of cyclisation or at any other appropriate moment in the synthesis. The protections and deprotections are then carried out as described above.

Another object of the invention is a method according to the above, characterised in that the compound of formula (II) is obtained by a method wherein a compound of formula (IV) is processed:

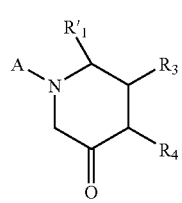
(IV)

wherein $R'_1$, $R_3$ and $R_4$ are defined as above, and A represents a hydrogen atom or a group protecting the nitrogen, by a reducing agent, in order to obtain a compound of formula (V):

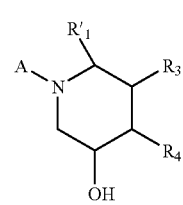
(V)

wherein A, $R'_1$, $R_3$ and $R_4$ keep the meanings mentioned above and $R_9$ represents a leaving group, that is processed with a compound of formula $Z_1H_2$ wherein $Z_1$ represents a protected —HN—OH group and then, if necessary, by a deprotection agent of the appropriate nitrogen atom.

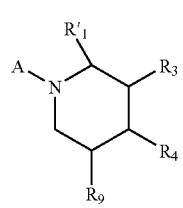
(VI)

A further object of the invention is a method according to the above, characterised in that the compound of formula (II) is obtained by a method wherein a compound of formula (IV) is processed as defined above, by hydroxylamine protected at the hydroxyl group, to obtain a compound of formula (VII):

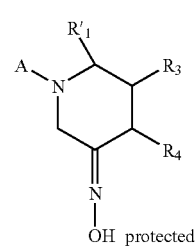
(VII)

wherein A, $R'_1$, $R'_2$, $R_3$, n and $R'_8$ are defined as above, and are made to react with a reducing agent in order to obtain a compound of formula (VIII):

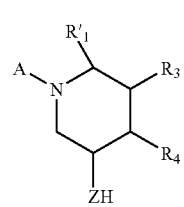
(VIII)

wherein A, $R'_1$, $R_3$, $R_4$, n" and ZH are defined as above, that is processed, if necessary, by a deprotection agent of the appropriate nitrogen atom.

The nitrogen protection agent is notably one of those mentioned above.

The reducing agent is notably an alkaline borohydride.

The leaving group is notably a sulphonate, for example un mesylate or a tosylate, obtained by action of the corresponding sulphonyl chloride in the presence of a base, or a halogen, more particularly chlorine, bromine or iodine, obtained for example by action of thionyl chloride or $P(C_6H_5)_3CBr_4$ or $PBr_3$ or, in the case of an iodine atom, by the action of an alkaline iodide on a sulphonate.

The deprotection agent is notably one of those mentioned above.

The reducing agent used on the compound of formula (VII) is notably a sodium cyano or acetoxyborohydride.

As indicated above, compounds of the general formula (I) possess an excellent antibiotic activity, against *Pseudomonas aeruginosa* and in the models of animal infection by strains resistant to commonly used anti-bacterial agents. This remarkable and unexpected antibiotic activity was not observed for the compounds described in the application WO 02/100860.

These properties render said compounds suitable, in free form, as zwitterions, or salts of pharmaceutically acceptable acids and bases for use as drugs in the treatment of severe *Pseudomonas* infections, notably nosocomial infections and, in general, major infections in subjects at risk. These can be particularly infections of the respiratory tract, for example acute pneumonia or chronic infections of the upper tracts, infections of the blood, for example septicaemias, acute or chronic infections of the urinary tract, infections of the auditory system, for example malignant external otitis, or suppurative chronic otitis, skin and soft tissue infections, for example dermatitis, infected wounds, folliculitis, pyroderma, the resistant forms of acne, eye infections, for example corneal ulcers, infections of the nervous system, notably meningitis and brain abscesses, cardiac infections such as endocarditis, infections of bones and joints such as sternoarticular pyoarthrosis, vertebral osteomyelitis, pubic symphysitis, infections of the gastro-intestinal tube, such as necrosing enterocolitis and peri-rectal infections.

Therefore an object of this invention is also compounds of formula (I) as defined above for use as drugs, and notably as antibiotics.

Among the compounds of formula (I), a notable object of the invention is the use as a drug of compounds wherein $R_3$ and $R_4$ together form a pyrazolyl or triazolyl heterocycle, optionally substituted, and among these, those in which $R_1$ is selected in the group composed of the groups $(CH_2)_n$—$NH_2$ and $(CH_2)_n$—$NHCH_3$, where n is as defined above, the heterocycle formed by $R_3$ and $R_4$ is substituted by a $(C_1$-$C_6)$ alkyl radical.

Among the compounds of formula (I), a particular object of the invention is the use as a drug of compounds wherein $R_1$ represents a $(CH_2)_n$—$NH_2$ or $(CH_2)_n$—$NHCH_3$, radical, where n is as defined above and $R_3$ and $R_4$ together form a pyrazolyl ring substituted by a $(C_1$-$C_6)$ alkyl radical.

Among the compounds of formula (I), a very particular object of the invention is the use as a drug of:
trans 8-(aminomethyl)-4,8-dihydro-1-methyl-6-oxo-5-(sulphooxy)-4,7-methano-7H-pyrazolo[3,4-e][1,3]diazepin-6(5H)-one,
trans 8-(aminomethyl)-4,8-dihydro-6-oxo-5-(sulphooxy)-4,7-methano-7H-pyrazolo[3,4-e][1,3]diazepin-6(5H)-one and
trans 8-(methylaminomethyl)-4,8-dihydro-6-oxo-5-(sulphooxy)-4,7-methano-7H-pyrazolo[3,4-e][1,3]diazepin-6(5H)-one,
in free form, as a zwitterion, and salts with pharmaceutically acceptable inorganic or organic bases and acids.

A further object of the invention is pharmaceutical compositions with, as active principle, at least one of the compounds according to the invention as defined above. These compositions can be administered by mouth, by rectum, parenterally, notably intramuscularly or locally by topical application on the skin and the mucosa.

The compositions according to the invention can be solid or liquid and present in pharmaceutical forms in current use in human medicine such as, for example, simple or coated tablets, capsules, granules, suppositories, injectable preparations, ointments, creams, gels; they are prepared according to the usual methods. The active principle or principles can be incorporated in the excipients usually used in these pharmaceutical compositions, such as talc, gum Arabic, lactose, starch, magnesium stearate, cocoa butter, aqueous or other media, fatty bodies of animal or plant origin, paraffin derivatives, glycols, different wetting, dispersing or emulsifying agents, preservatives.

These compositions can notably take the form of a lyophilisate designed to be dissolved as required in an appropriate solvent, for example pyrogen free sterile water.

The dose administered can vary depending on the condition being treated, the subject, the administration route and the product concerned. It can, for example, be comprised between 0.250 and 10 g per diem, by the oral route in humans, using the product described in example 1 or comprised between 0.25 and 10 g per diem by intramuscular or intravenous injection.

The products of formula (I) can also be used as disinfectants for surgical instruments.

The following examples illustrate the invention.

EXAMPLES

Example 1 sodium and trifluoroacetate salts of trans[[8-(aminomethyl)-4,8-dihydro-1-methyl-6-oxo-5-(sulfooxy)-4,7-methano-7H-pyrazolo[3,4-e][1,3]diazepin-6(5H)-one Stage A 4,7-dihydro-1-methyl-4-((phenylmethoxy)amino)-1H-pyrazolo[3,4-c]pyridine-6(5H), 7-dicarboxylate of 6-(1,1-dimethylethyl-ethyl) and 7-methyl (B)

Derivative A (4,7-dihydro-4-hydroxy-1-methyl-1H-pyrazolo[3,4-c]pyridine-6(5H), 7-dicarboxylate of 6-(1,1-dimethylethyl) and 7-methyl, described in the application WO 02100860 (10 g, 32.12 mmol) is put in suspension in dichloromethane (100 ml) at ambient temperature under nitrogen and with agitation. The suspension dissolves after triethylamine is added (14.30 ml, 10.28 mmol, 3.2 eq). A solution of methane sulphonyl chloride (11.4 ml, 96.36 mmol, 3 eq) in dichloromethane (12 ml, 1 volume) is added dropwise to the reaction medium cooled to −78° C. After 30 min contact, the alcohol A is completely transformed into mesylate.

A solution of O-benzyl-hydroxylamine in dichloromethane is freshly prepared from O-benzylhydroxylamine hydrochloride (25.4 g, 160.6 mmol, 5 eq). The O-benzylhydroxylamine hydrochloride is dissolved in a mixture of O-benzylhydroxylamine hydrochloride (100 ml) and water (50 ml). A solution of 2N caustic soda (85 ml, 176.66 mmol) is added at 0° C. After 10 min of contact and decantation, the organic phase is dried on magnesium phosphate for 45 min, then concentrated to half volume. The addition of this solution to the mesylate prepared above is done at −78° C. dropwise over 1 hour. The reaction mixture is agitated allowing the temperature to increase gradually to ambient. Water (200 ml)

is added and it is diluted with dichloromethane (100 ml), agitated, decanted then the aqueous phase is re-extracted with dichloromethane. The organic phase is washed with a saturated NaCl solution (200 ml), dried, then concentrated to dryness. A white amorphous powder is recovered, which after chromatography gives the B derivative expected (8.25 g, 66%).

MS (ES (+)): m/z=417.2

$^1$H NMR (400 MHz, CDCl3): one diastereoisomer (2 rotamers) δ (ppm)=1.43 (s, 9H, tBu), 3.15 (dd, 1H, N—CH2—CH—N), 3.68/3.70 (s, 3H, CH3), 3.84 (s, 3H, CH3), 3.98 (m, 2H, N—CH2—CH—N), 4.6-4.8 (massive, 3H, NH—O—CH2-Ph and N—CH2-CH—N), 5.40/5.8 (s, 1H, CH—CO2Me), 7.22-7.31 (massive, 5H, Ph), 7.40 (s, 1H, H pyrazole)

Stage B

Trans 1-methyl-6-oxo-5-(phenylmethoxy)-4,5,6,8-tetrahydro-4,7-methano-1H-pyrazolo[3,4-e][1,3]diazepine-8(7H) methyl carboxylate (C)

A 4N solution of HCl/dioxane (400 ml, 15 eq) is poured into a solution of B (21 g, 50.42 mmol) dissolved in dioxane (50 ml) at ambient temperature. The reaction mixture is agitated for 30 min, then the dioxane is evaporated. The residue is taken up while being agitated in a mixture of water (100 ml) and ethyl acetate (500 ml). A solution of ammonia concentrated to 20% (42 ml) is added at 0° C. The agitation is continued for 30 min. After decantation the aqueous phase is re-extracted with ethyl acetate (2*300 ml), and the last extraction is carried out after saturation of the aqueous phase with NaCl. The organic phase is dried then concentrated. The intermediate deprotected piperidine is obtained in the form of a yellow oil (m=15.7 g, 98%) that is taken up in acetonitrile (400 ml). To this mixture cooled to 0° C., are added triethylamine (21 ml, 151.2 mmol, 3 eq), then diphosgene (3.04 ml, 25.2 mmol, 0.5 eq) dropwise over 30 min. After a night in contact at ambient temperature, the medium is concentrated then taken up with ethyl acetate (500 ml) and treated with a 10% solution of tartaric acid (200 ml). The mixture is agitated and decanted. The organic phase is washed with a solution of 10% tartaric acid (2*200 ml), then with a solution of saturated NaCl, then dried and concentrated at reduced pressure. The white product obtained (m=15.3 g, 89%) is taken up in dichloromethane (150 ml). 1-8-diazabicyclo[5.4.0]undec-7-ene (7.53 ml, 50.04 mmol) is added dropwise. The mixture is agitated for 2 hours, treated with water (200 ml), agitated, decanted. The organic phase is washed with water (2*200 ml), then with a saturated NaCl solution (1*200 ml), and dried on MgSO$_4$, then concentrated to dryness.

The expected derivative C is recovered (m=14.72 g, 85%), in the form of a white solid.

MS (ES (+)): m/z [M$^+$]=343

$^1$H NMR (400 MHz, CDCl3): δ (ppm)=3.25 (d, 1H, N—CH2—CH—N), 3.45 (d, 1H, N—CH2-CH—N), 3.80 (s, 3H, CH3), 3.88 (s, 3H, CH3), 3.9 (s, 1H, N—CH2-CH—N), 4.7 (d, 1H, N—O—CH2-Ph), 5.02 (d, 1H, N—O—CH2-Ph), 5.22 (s, 1H, CH—CO2Me), 7.39-7.43 (massive, 6H, H pyrazole+Ph)

Stage C 4,8-dihydro-8-(hydroxymethyl)-1-methyl-5-(phenylmethoxy)-4,7-methano-7H-pyrazolo[3,4-e][1,3]diazepin-6(5H)-one (D)

A solution of C (5 g, 14.60 mmol) in an anhydrous mixture of tetrahydrofurane (150 ml)/methanol (50 ml), under nitrogen and agitated, is cooled −10° C. Lithium borohydride (668 mg, 30.67 mmol, 1.2 eq) is added to the reaction medium. After being agitated for 2 h at −10° C., 1.2 additional eq of LiBH$_4$ are added. The reaction is treated cold 2 h later with a solution of 10% NaH$_2$PO$_4$. The tetrahydrofurane and the methanol are evaporated under reduced pressure (200 mbar, 40° C.). The remaining mixture is taken up with ethyl acetate (200 ml), agitated and decanted. The aqueous phase is re-extracted with 100 ml ethyl acetate. The organic phase is dried on magnesium sulphate then concentrated to dryness. The pale yellow powder obtained (6.6 g) is chromatographed on silicon dioxide (eluent-ethyl acetate) to give the derivative D (3.2 g, 10.18 mmol, 64%).

MS (ES (+)) m/z [M$^+$]=315

$^1$H NMR (400 MHz, DMSO-$d_6$): δ (ppm)=3.16 (dd, 1H, N—CH2—CH—N), 3.48 (d, 1H, N—CH2-CH—N), 3.71 (s, 3H, CH3), 3.81-3.91 (massive, 2H, CH2OH), 4.44 (m, 1H, N—CH2-CH—N), 4.48 (m, 1H, CHCH2OH), 4.88 (m, 2H, N—O—CH2-Ph), 5.20 (m, 1H, OH), 7.35-7.40 (massive, 6H, H pyrazole+Ph).

Stage D

Trans 4,8-dihydro-1-methyl-8-[(methylsulfonyl)oxymethyl)]-5-(phenylmethoxy)-4,7-methano-7H-pyrazolo[3,4-e][1,3]diazepin-6(5H)-one (E)

Derivative D (2.76 g, 8.78 mmol) is dissolved in dichloromethane (100 ml) at ambient temperature under nitrogen with agitation. After cooling to 0° C., triethylamine (1.83 ml, 13.17 mmol, 1.5 eq) is added, then dropwise a solution of mesyl chloride (1.61 g, 14.05 mmol) in dichloromethane (100 ml). The ice bath is removed at the end of the addition. After one hour of contact at ambient temperature, the reaction is treated with a 10% solution of NaH$_2$PO$_4$ (80 ml) while agitating. After agitation and decantation, the aqueous phase is re-extracted with dichloromethane (50 ml). The organic phase is dried, then concentrated at reduced pressure to give the expected derivative (3.44 g, quantitative yield).

MS (ES (+)): m/z [M$^+$]=393

$^1$H NMR (400 MHz, DMSO-d$_6$): δ (ppm)=3.23 (dd, 1H, N—CH2-CH—N), 3.26 (s, 3H, CH3), 3.45 (d, 1H, N—CH2-CH—N), 3.76 (s, 3H, CH3), 4.52 (m, 1H, N—CH2-CH—N), 4.58 (dd, 1H, CH—CH2-OMs), 4.66 (dd, 1H, CH—CH2-OMs), 4.88 (m, 3H, CHCH2OMs and N—O—CH2-Ph), 7.35-7.45 (massive, 6H, H pyrazole+Ph).

Stage E trans 8-(azidomethyl)-4,8-dihydro-1-methyl-5-(phenylmethoxy)-4,7-methano-7H-pyrazolo[3,4-e][1,3]diazepin-6(5H)-one (F)

Sodium azide is added all at once (1.71 g, 26.3 mmol) to a solution of E (3.44 g, 8.78 mmol) in dimethylformamide (70 ml) at ambient temperature under nitrogen with agitation. The reaction medium is heated to 65° C. overnight, then treated with an aqueous solution of 10% NaH$_2$PO$_4$ (50 ml). After agitation and decantation, the aqueous phase is re-extracted with dichloromethane (2*50 ml). The organic phase is dried, then concentrated at reduced pressure to give the 3.96 g of the expected derivative F (3 g, 8.78 mmol).

MS (ES (+)): m/z [M$^+$]=340

$^1$H NMR (400 MHz, DMSO-d$_6$): δ (ppm)=3.20 (dd, 1H, N—CH2-CH—N), 3.48 (d, 1H, N—CH2-CH—N), 3.66 (dd, 1H, CH—CH2-N3), 3.72 (s, 3H, CH3), 3.92 (dd, 1H, CH—CH2-N3), 4.50 (d, 1H, N—CH2-CH—N), 4.76 (dd, 1H, CHCH2ON3), 4.89 (m, 2H, N—O—CH2-Ph), 7.35-7.45 (massive, 6H, H pyrazole+Ph).

Stage F trans[[4,8-dihydro-1-methyl-6-oxo-5-(phenyl-methoxy)-4,7-methano-7H-pyrazolo[3,4-e][1,3]diazepin-8-yl]methyl]-carbamate of 1,1-dimethylethyl (G)

A molar solution of trimethylphosphine (3.4 ml, 3.4 mmol) is added dropwise to a solution of F (1.15 g, 3.39 mmol) in a mixture of toluene (5 ml) and tetrahydrofurane (5 ml) at ambient temperature under nitrogen with agitation. After 3 h contact, a solution of BOC—ON (0.92 g, 3.6 mmol) in tetrahydrofurane (10 ml) is added dropwise to the reaction medium cooled to 0° C. The agitation is continued for 3 h at ambient temperature. The reaction medium is treated with a 10% aqueous solution of $NaHCO_3$ (50 ml). After agitation and decantation, the aqueous phase is re-extracted with ethyl acetate (50 ml). The organic phase is dried, then concentrated at reduced pressure to give 2.2 g of oil. The unrefined product is chromatographed on a silicon dioxide column (eluent cyclohexane/ethyl acetate 5/5). The expected product is obtained (0.62 g, 1.49 mmol, 70%).

MS (ES (+)): m/z [M$^+$]=414

$^1$H NMR (400 MHz, CDCl3): δ (ppm)=1.39 (s, 9H, tBu), 3.05 (dd, 1H, N—CH2-CH—N), 3.19 (dd, 1H, CH—CH2-NHBOC), 3.27 (dd, 1H, N—CH2-CH—N), 3.72 (s, 3H, CH3), 3.78 (m, 1H, CH—CH2—NHBOC), 3.88 (d, 1H, N—CH2-CH—N), 4.48 (dd, 1H, CHCH2NHBOC), 4.79 (d, 1H, N—O—CH2-Ph), 4.92 (d, 1H, N—O—CH2-Ph), 5.18 (m, 1H, H mobile), 7.35 (s, 1H, H pyrazole), 7.37-7.48 (massive, 5H, Ph)

Stage G

Pyridinium salt of trans[[4,8-dihydro-1-methyl-6-oxo-5-(sulphooxy)-4,7-methano-7H-pyrazolo[3,4-e][1,3]diazepin-8-yl]methyl]-carbamate of 1,1-dimethylethyl (H)

10% palladium on charcoal (140 mg) is added to a solution of G (0.6 g, 1.45 mmol) in methanol (10 ml). The reaction medium is hydrogenated for 3 h. The methanol is then evaporated at reduced pressure to give the debenzylated derivative.

MS (ES (+)): m/z [M$^+$]=324

The debenzylated intermediate is taken up in pyridine (3 ml) in the presence of pyridine/sulphur trioxide complex (462 mg, 2.9 mmol). The reaction is maintained under agitation at ambient temperature overnight. The medium is then concentrated at reduced pressure. The unrefined reaction product is chromatographed on a silicon dioxide column (eluent 100% dichloromethane then gradient with methanol from 5% to 20%) to give the derivative H (0.49 g, 1.25 mmol, 84%).

MS (ES (+)): m/z [M$^-$]=402

$^1$H NMR (400 MHz, DMSO-d$_6$): δ (ppm)=1.41 (s, 9H, tBu), 3.30-3.80 (massive, 4H, 2 CH2), 3.72 (s, 3H, CH3), 4.42 (dd, 1H, CHCH2ONHBOC), 4.64 (d, 1H, N—CH2-CH—N), 7.21 (m, 1H, H mobile), 7.35 (s, 1H, H pyrazole), 8.02 (dd, 2H, pyridine), 8.54 (m, 1H, pyridine), 8.91 (m, 2H, pyridine)

Stage H

Sodium salt of trans[[4,8-dihydro-1-methyl-6-oxo-5-(sulphooxy)-4,7-methano-7H-pyrazolo[3,4-e][1,3]diazepin-8-yl]methyl]-carbamatel of 1,1-dimethylethyl (I)

A suspension of 60 g of DOWEX 50WX8 resin in a solution of 2N caustic soda (300 ml) is agitated for one hour, then poured onto a chromatography column. It is eluted with demineralised water until pH neutral, then the column is conditioned with a 90/10 mixture of water/THF. Derivative H (0.49 g, 1.01 mmol) is dissolved in a minimum of water, placed on the column, then eluted with a 90/10 mixture of water/THF. The fractions containing the substrate are pooled and frozen. The frozen solution is lyophilised to lead to the expected product I (0.44 g, 1.03 mmol, 100%).

MS (ES (+)): m/z [M$^-$]=402

$^1$H NMR (400 MHz, DMSO-d$_6$): δ (ppm)=1.39 (s, 9H, tBu), 3.30-3.72 (m, 7H, 2 CH2, CH3), 4.42 (m, 1H, CHCH2ONHBOC), 4.64 (s, 1H, N—CH2-CH—N), 7.16 (m, 1H, H mobile), 7.35 (s, 1H, H pyrazole).

Stage I sodium and trifluoroacetate salt of trans[[8(aminomethyl)-4,8-dihydro-1-methyl-6-oxo-5-(sulphooxy)-4,7-methano-7H-pyrazolo[3,4-e][1,3]diazepin-6(5H)-one (J)

A solution of trifluoroacetic acid (10 ml) in dichloromethane (10 ml) is poured dropwise into a solution of I (0.15 g, 0.35 mmol) in dichloromethane (5 ml) under nitrogen and cooled to 0° C. The reaction is maintained under agitation for 1 h at ambient temperature. The mixture is evaporated to dryness and taken up in a minimum of water. The solution is frozen then lyophilised to give the expected derivative J (193 mg, 0.35 mmol, 100%).

MS (ES (+)): m/z [M$^-$]=301

$^1$H NMR (400 MHz, DMSO-d$_6$): δ (ppm)=3.32 (dd, 1H, N—CH2-CH—N), 3.33-3.37 (m, 2H, 2CH), 3.43 (d, 1H, N—CH2-CH—N), 3.74 (s, 3H, CH3), 4.73 (m, 2H, CH—CH2-NH3+), 7.41 (s, 1H, H pyrazole), 8.10 (m, 3H, NH3$^+$)

Example 2

The sodium and trifluoroacetate salt of trans[[8-(amino-methyl)-4,8-dihydro-6-oxo-5-(sulphooxy)-4,7-methano-7H-pyrazolo[3,4-e][1,3]diazepin-6(5H)-one

Stage A trans-8-(hydroxymethyl)-4,5,6,8-tetrahydro-6-oxo-5-(phenylmethoxy)-4,7-methano-7H-pyrazolo[3,4-e][1,3]diazepin-6(5H)-one The methyl ester of trans-4,5,6,8-tetrahydro-6-oxo-5-(phenylmethoxy)-4,7-methano-7H-pyrazolo[3,4-e][1,3]diazepine-8-carboxylate described in the application WO2004/052891 (Example 1, stage K) 5 g, 15.2 mmol) is dissolved in a 1/1 mixture of anhydrous methanol/tetrahydrofurane (100 ml), under nitrogen. NaBH$_4$ (2.3 g, 60.9 mmol) is then added little by little. The reaction medium is agitated at ambient temperature overnight, then treated with an aqueous solution of 10% $NaH_2PO_4$ (100 ml). After evaporating to dryness, the reaction mixture is taken up in water. The precipitate formed is agitated overnight in ice, then filtered and dried for at least 24 h in a vacuum in presence of $P_2O_5$, to give the expected compound (3.3 g, 11.0 mmol, 72%) in the form of a white powder.

MS (ES(+)): m/z [M$^+$]=301

$^1$H RMN (400 MHz, DMSO-d$_6$): δ (ppm)=3.18-3.50 (ABX, 2H, N—$CH_2$—CH—N), 3.65-3.76 (ABX, 2H, N—CH—$CH_2$—OH), 4.34 (t, 1H, N—CH—$CH_2$—OH), 4.46 (d, 1H, N—CH$_2$—CH—N), 4.88 (s, 2H, CH$_2$-Ph), 7.29-7.43 (m, 5H, Ph), 7.66 (s, 1H, H pyrazole), 12.72 (broad, 1H, OH).

Stage B trans[[4,8-dihydro-6-oxo-5-(phenylmethoxy)-4,7-methano-7H-pyrazolo[3,4-e][1,3]diazepin-8-yl]methyl]-carbamate of 1,1-dimethyl The alcohol obtained in stage A of example 2 (1.73 g, 5.76 mmol) is dissolved in anhydrous pyridine (35 ml), under nitrogen at 0° C. Methanesulphonyl chloride (1.78 ml, 23 mmol) is added dropwise. After 2 h30 of agitation at ambient temperature, the reaction medium is treated with a saturated aqueous solution of ammonium chloride (100 ml), then extracted with ethyl acetate. The combined organic phases are then washed 5 times with a saturated aqueous solution of ammonium chloride, dried on sodium sulphate, filtered then concentrated in a vacuum to give the expected dimesylated derivative in the form of a yellow oil.

The dimesylated intermediate is dissolved in anhydrous dimethylformamide (45 ml), under nitrogen, in the presence of sodium azide (1.12 g, 17.3 mmol). The reaction mixture is heated to 70° C. for 24 hours. If necessary, 1 eq of azide is added so that the conversion is complete. When the reaction is complete, the mixture is treated with a 10% aqueous solution of NaH$_2$PO$_4$ (100 ml) then extracted with dichloromethane. The combined organic phases are dried on sodium sulphate, filtered then concentrated in a vacuum to give the expected azide in the form of yellow oil.

The intermediate is put into reaction, under nitrogen, in absolute ethanol (17.5 ml). Then di-tert-butyl dicarbonate (1.38 g, 6.34 mmol), triethylsilane (1.38 ml, 8.64 mmol) and 10% palladium hydroxide on charcoal (52 mg) are added successively. After one night at ambient temperature, the reaction mixture is filtered then concentrated to give a crude yellow oil. This crude oil is purified by chromatography on a silicon dioxide column (eluent gradient CH2Cl2/MeOH 100/0 to 95/5 per 1%) to give the expected compounds (1.36 g, 3.40 mmol, 34%) as a white solid.

MS (ES(+)): m/z [M+]=401

1H RMN (400 MHz, MeOH-d4): δ (ppm)=1.51 (s, 9H, C(CH$_3$)$_3$), 3.21-3.59 (m, 4H, N—CH$_2$—CH—N et N—CH—CH$_2$—NHBoc), 4.36 (m, 1H, N—CH—CH$_2$—OH), 4.46 (m, 1H, N—CH$_2$—CH—N), 4.99 (AB, 2H, CH$_2$-Ph), 7.41-7.52 (m, 5H, Ph), 7.63 (s, 1H, H pyrazole).

Stage C trans[[4,8-dihydro-1-tert-butoxycarbamate-6-oxo-5-(phenylmethoxy)-4,7-methano-7H-pyrazolo[3,4-e][1,3]diazepin-8-yl]methyl]-carbamate of 1,1-dimethyl The compound obtained in stage B of example 2 (104 mg, 0.26 mmol) is dissolved in anhydrous dichloromethane (2.5 ml) then di-tert-butyl dicarbonate (114 mg, 0.52 mmol) and dimethylaminopyridine (32 mg, 0.26 mmol) are added to the mixture. After 1 night of agitation at ambient temperature, the reaction medium is treated with water The phases are separated then the organic phase is washed with a saturated aqueous solution of sodium chloride, dried on sodium sulphate, filtered then concentrated in a vacuum. The crude product thus obtained is purified by chromatography on silicon dioxide (eluent: CH2Cl2/AcOEt 90/10) to give the expected product (76 mg, 0.15 mmol, 59%).

MS (ES(+)): m/z [M+]=500

Stage D

Pyridinium salt of trans[[4,8-dihydro-1-tert-butoxycarbamate-6-oxo-5-(sulphooxy)-4,7-methano-7H-pyrazolo[3,4-e][1,3]diazepin-8-yl]methyl]-carbamate of 1,1-dimethyl The compound obtained in stage C of example 2 (76 mg, 0.15 mmol) is dissolved, under nitrogen, in an anhydrous mixture of dimethylformamide/CH$_2$Cl$_2$ 1/3 (0.87 ml). 10% palladium on charcoal at 50% in water (49 mg) is added. After three vacuum/nitrogen purges, the reaction mixture is placed in a hydrogen atmosphere until the starting product disappears in HPLC. The mixture is then concentrated in a vacuum then co-evaporated three times with anhydrous dichloromethane and then dried under reduced pressure in presence of P$_2$O$_5$ for 2 h.

The debenzylated derivative is taken up in anhydrous pyridine (0.43 ml), in nitrogen, in the presence of a pyridine/sulphur trioxide complex (48 mg, 0.30 mmol). The reaction mixture is agitated at ambient temperature until complete conversion in HPLC, then evaporated to dryness after treatment by adding water The crude product thus obtained is purified by chromatography on silicon dioxide (eluent: CH$_2$Cl$_2$/MeOH 90/10) to give the expected product (47 mg, 0.083 mmol 55%).

MS (ES(-)): m/z [M-2*BOC]=388

$^1$H RMN (400 MHz, MeOH-d$_4$): δ (ppm)=1.52 (s, 18H, 2×C(CH$_3$)$_3$), 3.50 (m, 4H, N—CH$_2$—CH—N et CH$_2$—NHBoc), 4.62 (m, 1H, CH—CH$_2$—NHBoc), 4.85 (d, 1H, N—CH$_2$—CH—N), 7.72 (s, 1H, H pyrazole).

Stage E

The sodium and trifluoroacetate salt of trans[[8-(amino-methyl)-4,8-dihydro-6-oxo-5-(sulphooxy)-4,7-methano-7H-pyrazolo[3,4-e][1,3]diazepin-6(5H)-one A suspension of 6 g of DOWEX 50WX8 resin in a solution of 2N caustic soda (30 ml) is agitated for 1 h, then poured onto a chromatography column. After washing with H$_2$O until pH neutral, the column is conditioned with a mixture of THF/H$_2$O 10/90. The compound obtained in stage D of example 2 (47 mg, 0.08 mmol) is dissolved in a minimum of methanol then placed on the column. After elution with a THF/H$_2$O 10/90 mixture, the fractions containing the expected product are pooled, frozen, then lyophilised to give the expected sodium salt.

The sodium salt is taken up in anhydrous dichloromethane (1.04 ml) in nitrogen then cooled to 0° C. A solution of trifluoroacetic acid/anhydrous dichloromethane 1/1 (2.04 ml) is added dropwise. The reaction mixture is then agitated at ambient temperature for 45 min. After evaporation to dryness then co-evaporation with anhydrous dichloromethane, the compound is taken up in water (~2 ml) then frozen and lyophilised to give the expected salt (16 mg, 0.030 mmol, 36%) in the form of a pale yellow powder.

MS (ES(-)): m/z [M$^-$]=288

$^1$H RMN (400 MHz, MeOH-d$_4$): δ (ppm)=3.37-3.69 (m, 4H, N—CH$_2$—CH—N et CH—CH$_2$—NH$_2$), 4.81 (dd, 1H, CH—CH$_2$—NH$_2$), 4.98 (d, 1H, N—CH$_2$—CH—N), 7.79 (s, 1H, H pyrazole).

Example 3

Sodium and trifluoroacetate salt of trans 8-(methylaminomethyl)-4,8-dihydro-1-methyl-5-(sulphooxy)-4,7-methano-7H-pyrazolo[3,4-e][1,3]diazepin-6(5H)-one

Stage A

Trans[[[4,5,6,8-tetrahydro-1-methyl-6-oxo-5(phenylmethoxy)-4,7-methano-7H-pyrazolo[3,4-e][1,3]diazepin-8-yl]methyl]-methylamino]trimethylphosphonium iodide A molar solution of trimethylphosphine (1.5 ml, 1.5 mmol) is added drop by drop to a solution of the derivative obtained in stage E of example 1 (0.5 g, 1.25 mmol) in solution in tetrahydrofuran (15 ml) at ambient temperature under nitrogen and agitation. After 2 h of agitation, methane iodide (0.21 g, 3.75 mmol) is added to the reaction medium. A light yellow precipitate quickly forms. After one night of agitation at ambient temperature, the reaction medium is concentrated under reduced pressure. The crude product is triturated in dichloromethane. The precipitate is filtered to give the expected product (0.42 g, 1.04 mmol, 84%) in the form of a yellowish iodine salt.

$^1$H NMR (400 MHz, CDCl$_3$) in the form of 2 conformers: δ (ppm)=2.04 (s, 3H, CH$_3$P), 2.32 (s, 3H, CH$_3$P), 2.35 (s, 3H, CH$_3$P), 3.03 (s, 3H, P═NCH$_3$ (A)-CH$_2$), 3.05 (s, 3H, P—N CH$_3$(B)-CH$_2$), 3.37 (m, 1H, N—CH$_2$—CH—N or CH—CH$_2$—N(CH$_3$)P), 3.44 (m, 1H, N—CH$_2$—CH—N or CH—CH$_2$—N(CH$_3$)P), 3.69 (m, 1H, N—CH$_2$—CH—N or CH—CH$_2$N(CH$_3$)P), 3.82 (s, 3H, CH$_3$), 3.88 (m, 1H, N—CH$_2$—CH—N or CH—CH$_2$—N(CH$_3$)P), 4.05 (d, 1H, N—CH$_2$—CH—N), 4.59 (d, 1H, CH—CH$_2$—N(CH$_3$)P), 4.88 (d, 1H, N—O—CH$_2$-Ph), 5.00 (d, 1H, N—O—CH$_2$-Ph), 7.35 (s, 1H, H pyrazole), 7.37-7.45 (massive, 5H, Ph)

Stage B

Trans 8-(methylaminomethyl)-4,8-dihydro-1-methyl-5-(phenylmethoxy)-4,7-methano-7H-pyrazolo[3,4-e][1,3]diazepin-6(5H)-one To an aqueous sodium carbonate solution (2.5N, 9 ml) is added the derivative obtained in stage A of example 3 (0.42 g, 1.04 mmol). The reaction medium is agitated at 55° C. for 3 h30. After cooling at ambient temperature, the reaction medium is saturated with sodium chloride in the presence of ethyl acetate (25 ml). The aqueous phase is extracted with ethyl acetate (3×25 ml). The organic phase is dried on magnesium sulphate then concentrated under reduced pressure to yield a yellow oil (0.26 g). The crude reaction product is purified by chromatography on a silica column (eluent dichloromethane 100% then methanol gradient from 2% to 10%) to give the expected derivative (0.084 g, 0.256 mmol, 26%).

MS (ES (+)): m/z [M+H]$^+$=328

$^1$H NMR (400 MHz, CDCl$_3$): δ (ppm)=2.97-3.00 (dd, 1H, N—CH$_2$—CH—N), 3.00 (CH—CH$_2$—NCH$_3$), 3.15 (dd, 1H, CH—CH$_2$—NCH$_3$), 3.9 (dd, 1H, N—CH$_2$—CH—N), 3.75 (s, 3H, CH$_3$), 3.98 (d, 1H, CH—CH$_2$—N(CH$_3$)Boc), 4.72 (dd, 1H, N—CH$_2$—CH—N), 4.90 (d, 1H, N—O—CH$_2$-Ph), 5.03 (d, 1H, N—O—CH$_2$-Ph), 7.30 (s, 1H, H pyrazole), 7.34-7.44 (massive, 5H, Ph)

Stage C

Trans[[4,5,6,8-tetrahydro-1-methyl-6-oxo-5-(phenylmethoxy)-4,7-methano-7H-pyrazolo[3,4-e][1,3]diazepin-8-yl]methyl]-methyl-carbamate of 1,1-dimethylethyl The derivative obtained in stage B of example 3 (80 mg, 0.244 mmol) is put in solution in dichloromethane (1 ml) and then at ambient temperature triethyl amine (60 µL, 0.488 mmol) and di-tert-butyl dicarbonate (106 mg, 0.488 mmol) are added successively. After 4 h of agitation at ambient temperature, a solution saturated with sodium chloride (5 ml) is added to the reaction medium. The aqueous phase is extracted by dichloromethane (3×20 ml). The organic phase is dried on magnesium sulphate then concentrated under reduced pressure to give an amorphous white powder (157 mg). The crude reaction product undergoes chromatography on a silica column (eluent dichloromethane 100% then ethyl acetate gradient from 20% to 30%) to give the expected derivative (0.068 g, 0.159 mmol, 60%).

MS (ES (+)): m/z [M+H]$^+$=428

$^1$H NMR (400 MHz, CDCl$_3$): δ (ppm)=1.59 (s, 9H, C(CH$_3$)$_3$), 3.05 (s, 3H, CH$_3$NBoc-CH$_2$), 3.10 (m, 3H, N—CH$_2$—CH—N, CH—CH$_2$-NBoc), 3.75 (m, 1H, N—CH$_2$—CH—N), 3.85 (s, 3H, CH$_3$), 3.99 (s, 1H, N—CH$_2$—CH—N), 4.75 (m, 1H, CH—CH$_2$—N(CH$_3$)Boc), 4.90 (d, 1H, N—O—CH$_2$-Ph), 5.02 (d, 1H, N—O—CH2-Ph), 7.37 (s, 1H, H pyrazole), 7.40-7.46 (massive, 5H, Ph)

Stage D

Pyridinium salt of trans[[4,5,6,8-tetrahydro-1-methyl-6-oxo-5-(sulphooxy)-4,7-methano-7H-pyrazolo[3,4-e][1,3]diazepin-8-yl]methyl]-methyl-carbamate of 1,1-dimethylethyl While proceeding as indicated in stage G of example 1, the compound obtained in stage C of example 3 (0.068 g, 0.159 mmol) in methanol (5 ml), in the presence of 10% palladium on carbon (25 mg) leads to the debenzylated product.

MS (ES (+)): m/z [M+H]$^+$=337

The debenzylated intermediate, pyridine (1 ml), pyridine/sulphur trioxide complex (50 mg, 0.318 mmol) lead to the expected salt (0.045 g, 0.090 mmol, 100%).

MS (ES (−)): m/z [M−H]$^-$=416

$^1$H NMR (400 MHz, MeOH-d$_4$) in the form of 2 conformers: δ (ppm)=1.53 (s, 9H, C(CH$_3$)$_3$, 3.09 (s, 3H, CH$_3$(A)NHBoc), 3.10 (s, 3H, CH$_3$(B)NHBoc), 3.37 (m, 1H, BocN(CH$_3$)—CH$_2$—CH or N—CH$_2$—CH—N), 3.58 (m, 1H, BocN(CH$_3$)—CH$_2$—CH or N—CH$_2$—CH—N), 3.75 (s, 3H, CH$_3$), 3.84 (m, 1H, BocN(CH$_3$)—CH$_2$—CH or N—CH$_2$—CH—N), 3.90 (m, 1H, BocN(CH$_3$)—CH$_2$—CH or N—CH$_2$—CH—N), 4.90 (m, 2H, N—CH—CH$_2$—N, N—CH$_2$—CH—N+signal H$_2$O), 7.54 (s, 1H, H pyrazole), 8.16 (dd, 2H, pyridine), 8.70 (dd, 2H, pyridine), 8.94 (d, 1H, pyridine)

Stage E

Sodium salt of trans[[4,5,6,8-tetrahydro-1-methyl-6-oxo-5-(sulphooxy)-4,7-methano-7H-pyrazolo[3,4-e][1,3]diazepin-8-yl]methyl]-methyl-carbamate of 1,1-dimethylethyl While proceeding as indicated in stage H of example 1, the salt obtained in stage D of example 3 (0.045 g, 0.090 mmol), DOWEX 50WX8 resin (30 g) and 2N soda (150 ml) lead to the expected sodium salt (0.039 g, 0.090 mmol, 100%).

MS (ES (−)): m/z [M−H]⁻=416

$^1$H NMR (400 MHz, MeOH-d$_4$) in the form of 2 conformers: δ (ppm)=1.56 (s, 9H, C(CH$_3$)$_3$), 3.09 (s, 3H, CH$_3$(A)NHBoc), 3.10 (s, 3H, CH$_3$(B)NHBoc), 3.37 (m, 1H, BocN(CH$_3$)—CH$_2$—CH or N—CH$_2$—CH—N), 3.64 (m, 1H, BocN(CH$_3$)—CH$_2$—CH or N—CH$_2$—CH—N), 3.75 (s, 3H, CH$_3$), 3.84 (m, 1H, BocN(CH$_3$)—CH$_2$—CH or N—CH$_2$—CH—N), 3.93 (m, 1H, BocN(CH$_3$)—CH$_2$—CH or N—CH$_2$—CH—N), 4.90 (m, 2H, N—CH—CH$_2$—N, N—CH$_2$—CH—N+signal H$_2$O), 7.55 (s, 1H, H pyrazole).

Stage F

Sodium and trifluoroacetate salt of trans 8-(methylaminomethyl)-4,8-dihydro-1-methyl-5(sulphooxy)-4,7-methano-7H-pyrazolo[3,4-e][1,3]diazepin-6 (5H)-one While proceeding as indicated in stage I of example 1, the sodium salt obtained in stage E of example 3 (0.039 g, 0.088 mmol), dichloromethane (5 ml) and a mixture of trifluoroacetic acid/anhydrous dichloromethane 1/1 (4 ml) lead to the expected product (39 mg, 0.08 mmol, 100%).

MS (ES (−)): m/z [M−H]⁻=315

$^1$H NMR (400 MHz, DMSO-d$_6$): δ (ppm)=2.76 (s, 3H, CH3NH$^+$$_2$—CH$_2$), 3.30-3.50 (m, 4H, N—CH$_2$—CH—N, NH$^+$$_2$—CH$_2$—CH), 3.75 (s, 3H, CH$_3$), 4.74 (m, 1H, N—CH$_2$—CH—N), 4.82 (d, 1H, CH—CH$_2$—NH$^+$$_2$CH$_3$), 7.43 (s, 1H, H pyrazole), 8.67 (m, 2H, NH$_3^+$)

Example 4

Pharmaceutical Composition

A composition for injection was prepared comprising:
The compound of example 1: 500 mg
Sterile aqueous excipient: q.s.p. 5 cm³
Pharmacological Study of the Products of the Invention
In Vitro Activity, Dilution Methods in Liquid Medium:

A series of tubes are prepared in which equal quantities of sterile nutrient medium are placed, and increasing quantities of the product being studied are placed in each tube then each tube is plated with a bacterial strain. After 24 hours incubation in an oven at 37° C., the growth inhibition is assessed by transillumination, which makes it possible to determine the minimum inhibition concentrations (MIC) expressed in μg/ml.

Tests are carried out in this way with the products of Examples 1 and 2 and compared with the products of Examples and 19 of application WO 02/100860. The products of Examples 1 and 2 are revealed to be very active against Pseudomonas aeruginosa, which is not at all the case for the compared products.

| Activity against Pseudomonas aeruginosa (comparison with the other examples) (MIC (μg/ml) 24 h) | Compound of Ex 1 | Compound of Ex 2 | Pyrazole amide (Ex 19 PCT Application WO 02/100860) | Pyrazole ester (Ex 18 PCT Application WO 02/100860) |
|---|---|---|---|---|
| 1771 strains wild type | 0.12 | 0.25 | >32 | >32 |

| Pseudomonas aeruginosa strain expriming resistant mechanism (MIC (μg/ml) 24 h) | Compound of Ex 1 | Compound of Ex 2 | Imipenem | Ceftazidine |
|---|---|---|---|---|
| 1771 strains wild type | 0.12 | 0.25 | 1 | 1 |
| PA01 wild type | 1 | — | 1 | 2 |
| Resisting via β-lactamases [8 strains] | 1-2 | 0.25-1 | 2-32 | 2-32 |
| Resisting via efflux pumps [11/5 strains] | 0.5-4/ 0.25-0.5 | —/0.5-1 | 0.25-4 | <=0.03-8 |
| Resisting via porin mutations [1 strain] | 2 | — | 16 | 2 |

The invention claimed is:

1. A compound represented by formula (I)

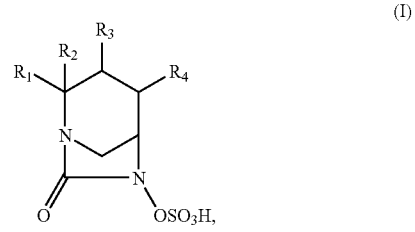

wherein R$_1$ represents a (CH$_2$)$_n$—NHR radical, where R is a (C$_1$-C$_6$)alkyl and n is equal to 1 or 2;

R$_2$ represents a hydrogen atom;

R$_3$ and R$_4$ together form an aromatic nitrogenated heterocycle with 5 apexes with 1, 2 or 3 nitrogen atoms optionally substituted by one or several R' groups, R' being selected from the group consisting of a hydrogen atom and alkyl radicals with 1 to 6 carbon atoms;

or a pharmaceutically acceptable salt or zwitterion thereof.

2. The compound of claim 1, wherein R$_3$ and R$_4$ together form an optionally substituted pyrazolyl or triazolyl radical.

3. The compound of claim 1, wherein R$_1$ is selected from the group consisting of (CH$_2$)$_n$—NH$_2$ and (CH$_2$)$_n$—NHCH$_3$; and the heterocycle formed by R$_3$ and R$_4$ is substituted by a (C$_1$-C$_6$) alkyl radical.

4. The compound of claim 1, wherein R$_1$ represents a (CH$_2$)$_n$—NH$_2$ or (CH$_2$)$_n$—NHCH$_3$; and R$_3$ and R$_4$ form a pyrazolyl ring substituted by a (C$_1$-C$_6$) alkyl radical.

5. A compound selected from the following group:
trans 8-(aminomethyl)-4,8-dihydro-1-methyl 5(sulphooxy)-4,7-methano-7H-pyrazolo[3,4-e][1,3]diazepin-6(5H)-one;
trans 8-(aminomethyl)-4,8-dihydro 5 -(sulphooxy)-4,7-methano-7-H-pyrazolo[3,4-e][1,3]diazepin-6(5H)-one; and
trans 8-(methylaminomethyl)-4,8-dihydro 5 -(sulphooxy)-4,7-methano-7H-pyrazolo[3,4-e][1,3]diazepin-6(5H)-one; or a pharmaceutically acceptable salt or zwitterion thereof.

6. A method for preparing a compounds of formula (I), comprising the steps of:

a) reacting a compound of formula (II) with a carbonylating agent, if necessary in the presence of a base:

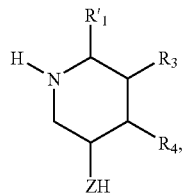

wherein:

$R'_1$ represents a CN, protected COOH, COOR or $(CH_2)_n R'_5$ radical;

$R'_5$ is a protected OH, CN, $NH_2$ or protected NHR, protected $CO_2H$, $CO_2R$ radical;

R is a $(C_1-C_6)$alkyl;

n is equal to 1 or 2;

$R_3$ and $R_4$ together form an aromatic nitrogenated heterocycle with 5 apexes with 1, 2 or 3 nitrogen atoms optionally substituted by one or several R' groups, R'being selected from the group consisting of a hydrogen atom and alkyl radicals with 1 to 6 carbon atoms; wherein the aminoalkyl substituents optionally present on the heterocycle formed by $R_3$ and $R_4$ being protected if necessary;

ZH represents a protected —NHOH group;

thereby forming an intermediate compound with the formula (III):

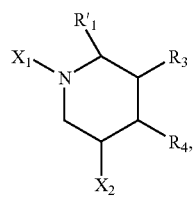

wherein either $X_1$ is a hydrogen atoms or a protecting group and $X_2$ represents a —Z—CO—$X_3$ group, wherein $X_3$ represents the rest of the carbonylating agent, or $X_2$ is a —ZH group and $X_1$ represents a CO—$X_3$ group, wherein $X_3$ represents the rest of the carbonylating agent;

b) cyclising the intermediate compound represented by formula (III) in the presence of a base; and c) completing, if necessary, one or several of the following reactions:
protection of the reactive functions,
deprotection of the reactive functions,
esterification,
saponification,
sulphatation,
ester reduction,
alkylation,
carbamoylation,
formation of an azido group,
reduction of an azido into an amine,
salification,
ion exchange, dividing or separating the diastereoisomers; either before step a) or after step b), or both, thereby forming the compound represented by formula (I).

7. The method of claim 6, wherein the carbonylation agent is selected from the group consisting of phosgene, diphosgene, triphosgene, aryl, aralkyl, alkyl and alkenyl chloroformiates, alkyl dicarbonates, carbonyl-diimidazole and mixtures thereof.

8. The method of claim 6, wherein the carbonylation reaction takes place in the presence of an amine.

9. The method of claims 6, further comprising the steps of:

a) reacting a compound of formula (IV) with a reducing agent:

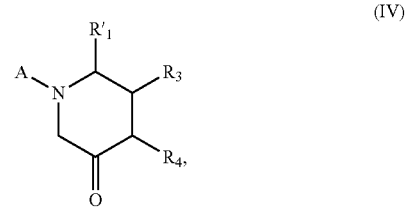

wherein A represents a hydrogen atom or a group protecting the nitrogen, thereby forming a compound of formula (V):

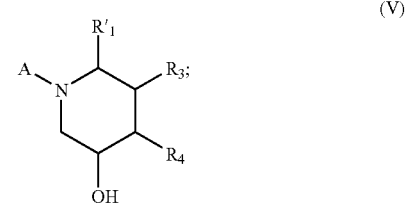

b) substituting if necessary, the OH group in the compound represented by formula (V) with a leaving group represented by $R_9$, thereby forming a compound of formula (VI):

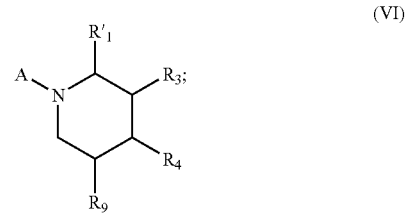

c) reacting the compound of formula (VI) with a compound of formula $Z_1H_2$ wherein $Z_1$ represents a protected —HN—OH group and, if necessary, deprotecting the nitrogen atom of the compound represented by formula (VI) with a deprotection agent, thereby forming the compound represented by formula (II).

10. The method of claim 6 further comprising the steps of:

a) reacting a compound of formula (IV) with hydroxylamine protected at the hydroxyl group:

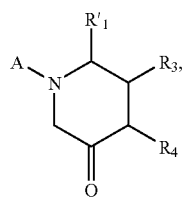

thereby forming a compound of formula (VII):

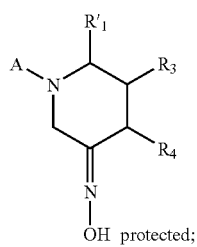

b) reacting the compound of formula (VII) with a reducing agent, thereby forming a compound of formula (VIII):

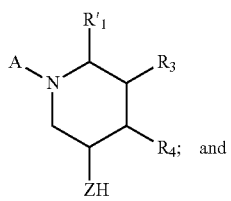

c) deprotecting the nitrogen atom, if necessary, with a deprotection agent, thereby forming a the compound represented by formula (II).

11. A method of treating a bacterial infection in a patient comprising the step of administrating the compound of claim 1, or a pharmaceutically acceptable salts thereof.

12. A method of treating a bacterial infection in a patient comprising the step of administrating the compound of claim 5, or a pharmaceutically acceptable salt thereof.

13. A pharmaceutical compound containing the compound of claim 1.

14. The compound of claim 2, wherein $R_1$ is selected from the group consisting of $(CH_2)_n$—$NH_2$ or $(CH_2)_n$—$NHCH_3$; and the heterocycle formed by $R_3$ and $R_4$ is substituted by a $(C_1$-$C_6)$ alkyl radical.

15. The compound of claim 3, wherein $R_1$ represents $(CH_2)_n$—$NH_2$ or $(CH_2)_{n\ —NHCH3}$; and $R_3$ and $R_4$ form a pyrazolyl ring substituted by a $(C_1$-$C_6)$ alkyl radical.

16. The method of claim 7, wherein the carbonylation reaction takes place in the presence of an amine.

17. A method of treating a bacterial infection in a patient comprising the step of administrating the compound of claim 2, or a pharmaceutically acceptable salt thereof.

18. A method of treating a bacterial infection in a patient comprising the step of administrating the compound of claim 3, or a pharmaceutically acceptable salt thereof.

19. A method of treating a bacterial infection in a patient comprising the step of administrating the compound of claim 4, or a pharmaceutically acceptable salt thereof.

20. A pharmaceutical composition comprising a pharmaceutically acceptable carrier or diluent and a compound selected from the group consisting of
  trans 8-(aminomethyl)-4,8-dihydro-1-methyl-5(sulphooxy)-4,7-methano-7H-pyrazolo[3,4-e][1,3]diazepine-6(5H) one;
  trans 8-(aminomethyl)-4,8-dihydro-6-oxo-5-(sulphooxy)-4,7-methano-7H-pyrazolo[3,4-e][1,3]diazepine-6(5H) one; and
  trans 8-(methylaminomethyl)-4,8-dihydro-5-(sulphooxy)-4,7-methano-7H-pyrazolo[3,4-e][1,3]diazepine-6(5) one; or a pharmaceutically acceptable salt or zwitterion thereof.

* * * * *

UNITED STATES PATENT AND TRADEMARK OFFICE
CERTIFICATE OF CORRECTION

| | | |
|---|---|---|
| PATENT NO. | : 8,063,219 B2 | Page 1 of 1 |
| APPLICATION NO. | : 12/595120 | |
| DATED | : November 22, 2011 | |
| INVENTOR(S) | : Maxime Lampilas et al. | |

It is certified that error appears in the above-identified patent and that said Letters Patent is hereby corrected as shown below:

IN THE CLAIMS:

In Claim 1, col. 20, line 37, <u>after</u> "represents a $(CH_2)_n$" and <u>before</u> "- NHR," insert -- $-NH_2$ or $(CH_2)_n$ --;

In Claim 5, col. 20, lines 56-57, <u>after</u> "8-(aminomethyl)-4,8-dihydro-1-methyl" and <u>before</u> "5 (sulphooxy)," insert -- "-" --;

In Claim 6, col. 21, line 46, replace "atoms" with -- atom --;

In Claim 9, col. 22, line 12, replace "claims" with -- claim --;

In Claim 15, col. 24, line 14, delete "$(CH_2)_{n\text{-}NHCH3}$" and add -- $(CH_2)_n\text{-}NHCH_3$ --.

Signed and Sealed this
Thirty-first Day of January, 2012

David J. Kappos
*Director of the United States Patent and Trademark Office*